(12) United States Patent
Cakmak et al.

(10) Patent No.: US 11,592,236 B2
(45) Date of Patent: Feb. 28, 2023

(54) CONTINUOUS ROLL-TO-ROLL FREEZE-DRYING SYSTEM AND PROCESS

(71) Applicant: Purdue Research Foundation, West Lafayette, IN (US)

(72) Inventors: Mukerrem Cakmak, Lafayette, IN (US); Alina Alexeenko, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/526,080

(22) Filed: Nov. 15, 2021

(65) Prior Publication Data
US 2022/0074662 A1     Mar. 10, 2022

Related U.S. Application Data

(62) Division of application No. 16/338,532, filed as application No. PCT/US2017/055933 on Oct. 10, 2017, now Pat. No. 11,175,092.
(Continued)

(51) Int. Cl.
*F26B 5/06* (2006.01)
*F26B 13/24* (2006.01)
(Continued)

(52) U.S. Cl.
CPC ............. *F26B 5/06* (2013.01); *A23L 3/44* (2013.01); *A61K 9/19* (2013.01); *F26B 13/24* (2013.01);
(Continued)

(58) Field of Classification Search
CPC .... A23L 3/44; A23L 3/48; A23L 3/485; F26B 5/06; F26B 13/24; F26B 5/04;
(Continued)

(56) References Cited

U.S. PATENT DOCUMENTS 3,222,237 A * 12/1965 Mckelvy ............... B29C 70/506
                                                                  428/110
3,253,420 A *  5/1966 De George ............... A23F 5/32
                                                                  426/524
(Continued)

FOREIGN PATENT DOCUMENTS

JP         58111662 A  *  7/1983
WO    WO-2019093397 A1 *  5/2019  ............... A23L 3/36
WO    WO-2019103731 A1 *  5/2019  ............ F26B 17/023

*Primary Examiner* — Edelmira Bosques
*Assistant Examiner* — Bao D Nguyen
(74) *Attorney, Agent, or Firm* — Hartman Global IP Law; Gary M. Hartman; Domenica N. S. Hartman

(57) ABSTRACT

Roll-to-roll freeze-drying (lyophilization) system and process for facilitating freeze-drying processes and enabling the collection of data by which a freeze-drying process can be monitored and evaluated. Such a system includes a roll-to-roll freeze-drying apparatus adapted to continuously freeze and dry a liquid to form a freeze-dried and encapsulate freeze-dried sheet portions of the freeze-dried sheet to create premeasured pouches containing the freeze-dried sheet portions. The system further includes a metrology section that monitors any of the freeze-dried sheet and the freeze-dried sheet portions during the freezing and drying of the liquid to generate data for controlling the freezing and drying of the liquid.

9 Claims, 7 Drawing Sheets

Related U.S. Application Data

(60) Provisional application No. 62/406,298, filed on Oct. 10, 2016.

(51) Int. Cl.

| | | |
|---|---|---|
| *A23L 3/44* | (2006.01) | |
| *A61K 9/19* | (2006.01) | |
| *G01N 30/72* | (2006.01) | |
| *G01N 30/86* | (2006.01) | |

(52) U.S. Cl.
CPC ......... *G01N 30/72* (2013.01); *G01N 30/8675* (2013.01)

(58) Field of Classification Search
CPC ............ F26B 5/047; F26B 5/065; A61K 9/19; G01N 30/8675; G01N 30/72; B32B 27/06; A23B 4/037; A23B 5/03; A23B 7/024; B05C 5/0254; B29C 41/28; A23F 5/32
USPC .......................................................... 34/287
See application file for complete search history.

(56) References Cited

U.S. PATENT DOCUMENTS

| | | | | |
|---|---|---|---|---|
| 3,257,483 A * | 6/1966 | Eberle | ................ | D06N 7/0086 425/115 |
| 3,585,099 A * | 6/1971 | Van Buskirk | ......... | B29C 70/603 427/206 |
| 3,702,779 A * | 11/1972 | Fadner et al. | ......... | D21H 25/06 156/80 |
| 4,104,807 A * | 8/1978 | Braun | ....................... | F26B 5/06 34/92 |
| 4,531,373 A * | 7/1985 | Rubinsky | ................ | A01N 1/02 62/65 |
| 5,183,600 A * | 2/1993 | Scher | ..................... | B29C 41/28 264/495 |
| 5,343,672 A * | 9/1994 | Kearney | ................ | B32B 15/20 53/343 |
| 5,457,895 A * | 10/1995 | Thompson | ........... | A61K 9/2072 34/296 |
| 5,462,743 A * | 10/1995 | Turner | ................ | A61K 9/7084 602/41 |
| 5,709,913 A * | 1/1998 | Andersen | ................ | B29C 51/04 428/152 |
| 5,756,993 A * | 5/1998 | Yoshinari | .............. | H01J 49/025 250/281 |
| 6,372,046 B1* | 4/2002 | Gottwald | ............... | D21H 23/40 118/410 |
| 2005/0150195 A1* | 7/2005 | Taylor | ................... | B29C 65/305 53/512 |
| 2008/0075837 A1* | 3/2008 | Bower | .................. | B41M 3/006 427/256 |
| 2009/0061331 A1* | 3/2009 | Nakano | ............... | G03F 7/70341 250/363.01 |
| 2009/0286098 A1* | 11/2009 | Yajima | ..................... | C08J 7/046 264/1.6 |
| 2010/0247612 A1* | 9/2010 | Fuisz | ....................... | A24B 3/18 424/443 |
| 2016/0079533 A1* | 3/2016 | Gabel | .................. | B05C 5/0254 118/712 |
| 2018/0047559 A1* | 2/2018 | Kamiya | ............ | H01L 21/67051 |
| 2019/0128608 A1* | 5/2019 | Jorgenson | ............. | F26B 17/008 |
| 2019/0277817 A1* | 9/2019 | Yamaguchi | ............. | G01N 30/86 |

\* cited by examiner

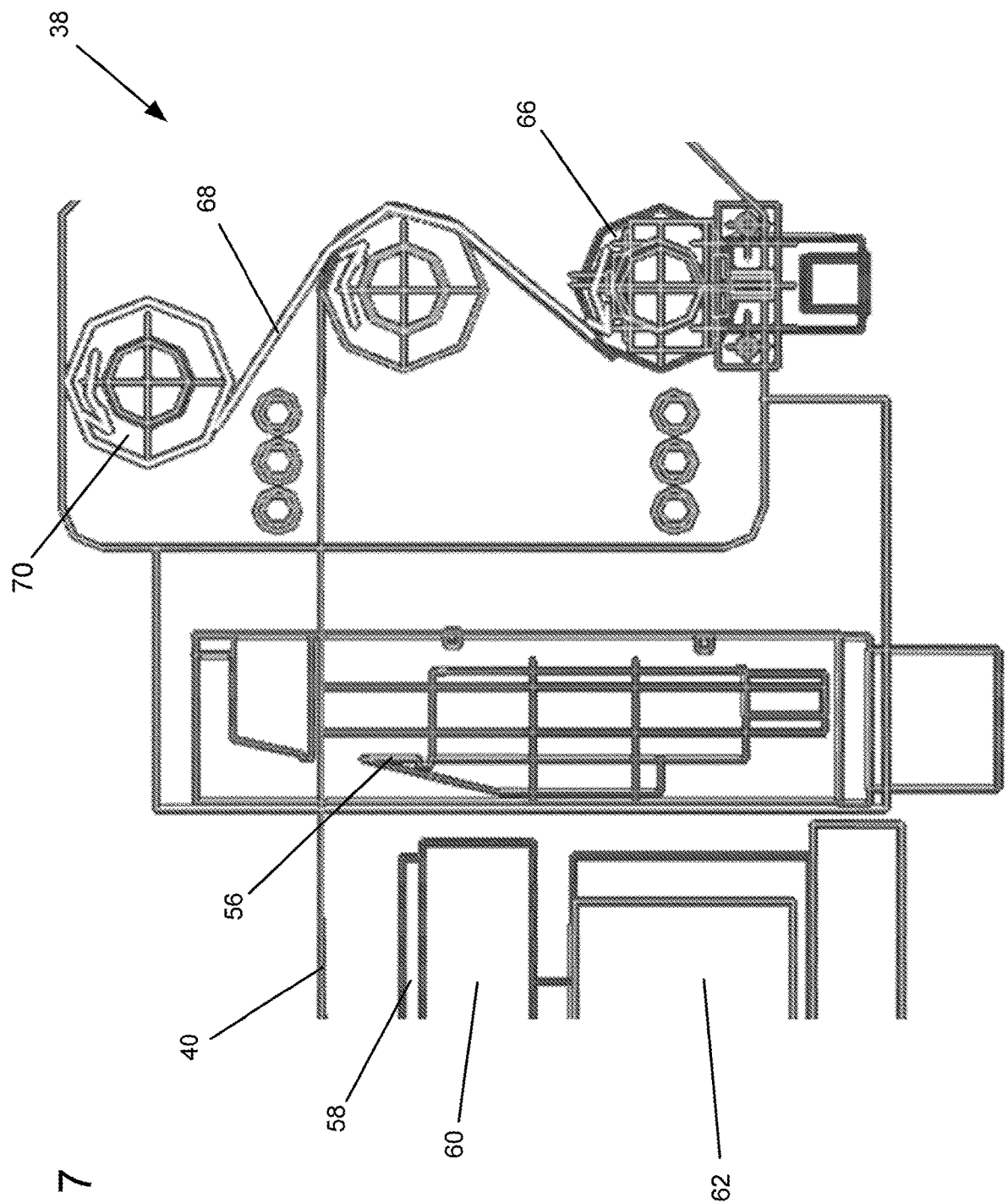

CONTINUOUS ROLL-TO-ROLL FREEZE-DRYING SYSTEM AND PROCESS

CROSS REFERENCE TO RELATED APPLICATIONS

This is a division patent application of co-pending U.S. patent application Ser. No. 16/338,532, filed Apr. 1, 2019, which claims the benefit of U.S. Provisional Application No. 62/406,298, filed Oct. 10, 2016. The contents of these prior applications are incorporated herein by reference.

BACKGROUND OF THE INVENTION

The present invention generally relates to freeze-drying processes. The invention particularly relates to processes and systems capable of freeze-drying items that are perishable or otherwise degrade over time, including but not limited to pharmaceuticals and food products.

Lyophilization (cryodesiccation), more commonly known as freeze-drying, is a well-known technique for stabilizing or preserving items that are perishable or otherwise degrade over time, notable examples of which include pharmaceuticals and foodstuffs. Freeze-drying processes generally involve dehydrating an item by freezing the item, and then reducing the surrounding pressure so that frozen water in the item is removed by sublimation, i.e., from the solid phase to the gas phase.

Freeze-drying of pharmaceuticals and foodstuffs are typically carried out by batch processing routes. There is an increasing interest by industry, particularly pharmaceutical companies, to switch from batch to continuous processes. In addition there is also a desire to obtain pristine physical and chemical (physicochemical) data during freeze-drying processes, including the sublimation rate (weight change), thicknesses, surface topology of ice, and the chemical composition of sublimated gas.

BRIEF DESCRIPTION OF THE INVENTION

The present invention provides a roll-to-roll freeze-drying (lyophilization) system capable of facilitating and further automating freeze-drying processes, while also enabling the collection of data by which a freeze-drying process can be monitored and evaluated.

According to one aspect of the invention, a continuous roll-to-roll freeze-drying system includes a roll-to-roll freeze-drying apparatus adapted to continuously freeze and dry a liquid to form a freeze-dried sheet and encapsulate freeze-dried sheet portions of the freeze-dried sheet to create premeasured pouches containing the freeze-dried sheet portions. The system further includes a metrology section that monitors the freeze-dried sheet and the freeze-dried sheet portions during the freezing and drying of the liquid to generate data for controlling the freezing and drying of the liquid.

Other aspects of the invention include a continuous roll-to-roll freeze-drying process that includes continuously freezing and drying a liquid to form a freeze-dried sheet and encapsulate freeze-dried sheet portions of the freeze-dried sheet to create premeasured pouches containing the freeze-dried sheet portions. The process has the further capability of monitoring any of the freeze-dried sheets and the freeze-dried sheet portions during the freezing and drying of the liquid to generate data for controlling the freezing and drying of the liquid.

Technical aspects of the methods and equipment described above preferably include the ability to provide rapid freeze-drying of pharmaceuticals and food stuffs by casting and freezing a thin sheet of liquid, followed by sublimation at programmable temperature and vacuum levels, to yield freeze-dried portions in premeasured amounts that are suitable for distribution in the marketplace.

Other aspects and advantages of this invention will be further appreciated from the following detailed description.

BRIEF DESCRIPTION OF DRAWINGS

FIG. 7 schematically represents a detailed front view of a take-up system of the freeze-drying apparatus of FIG. 3.

DETAILED DESCRIPTION OF THE INVENTION

Figure 1:
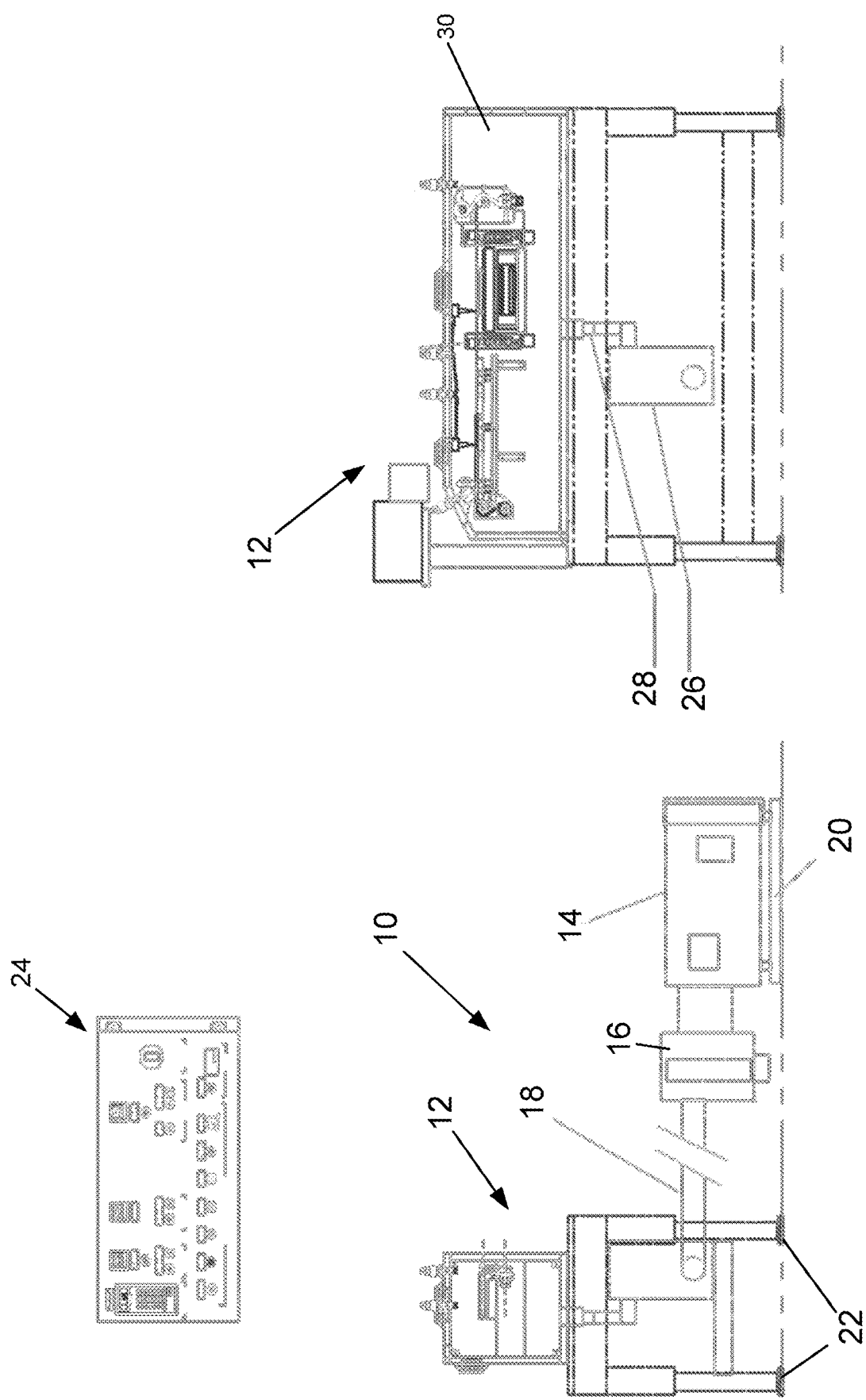
FIG. 1A schematically represents a side view of a roll-to-roll freeze-drying system that includes a freeze-drying apparatus connected to a vacuum pump in accordance with a nonlimiting embodiment of the invention, and represents.
FIG. 1B is a front view of the freeze-drying apparatus of FIG. 1A.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

In this disclosure, a continuous roll-to-roll freeze-drying (lyophilization) system 10 is provided that provides a continuous freeze-drying process, and also is capable of collecting physical and chemical (physicochemical) data relating to a freeze-drying process, and in particular physicochemical changes that take place during lyophilization, nonlimiting examples of which include sublimation rates (weight change), thicknesses, surface topologies, and chemical compositions of sublimated gas. As such, the system 10 is capable of monitoring a freeze-drying process to provide a fuller understanding of the process and its parameters, and to enhance throughput and quality control. Though the system 10 will be described as particularly well suited for freeze-drying perishable items or items that otherwise degrade over time, for example, pharmaceuticals and foodstuffs, it will be understood that the system 10 can be employed to freeze-dry a variety of different materials.

Figure 2:
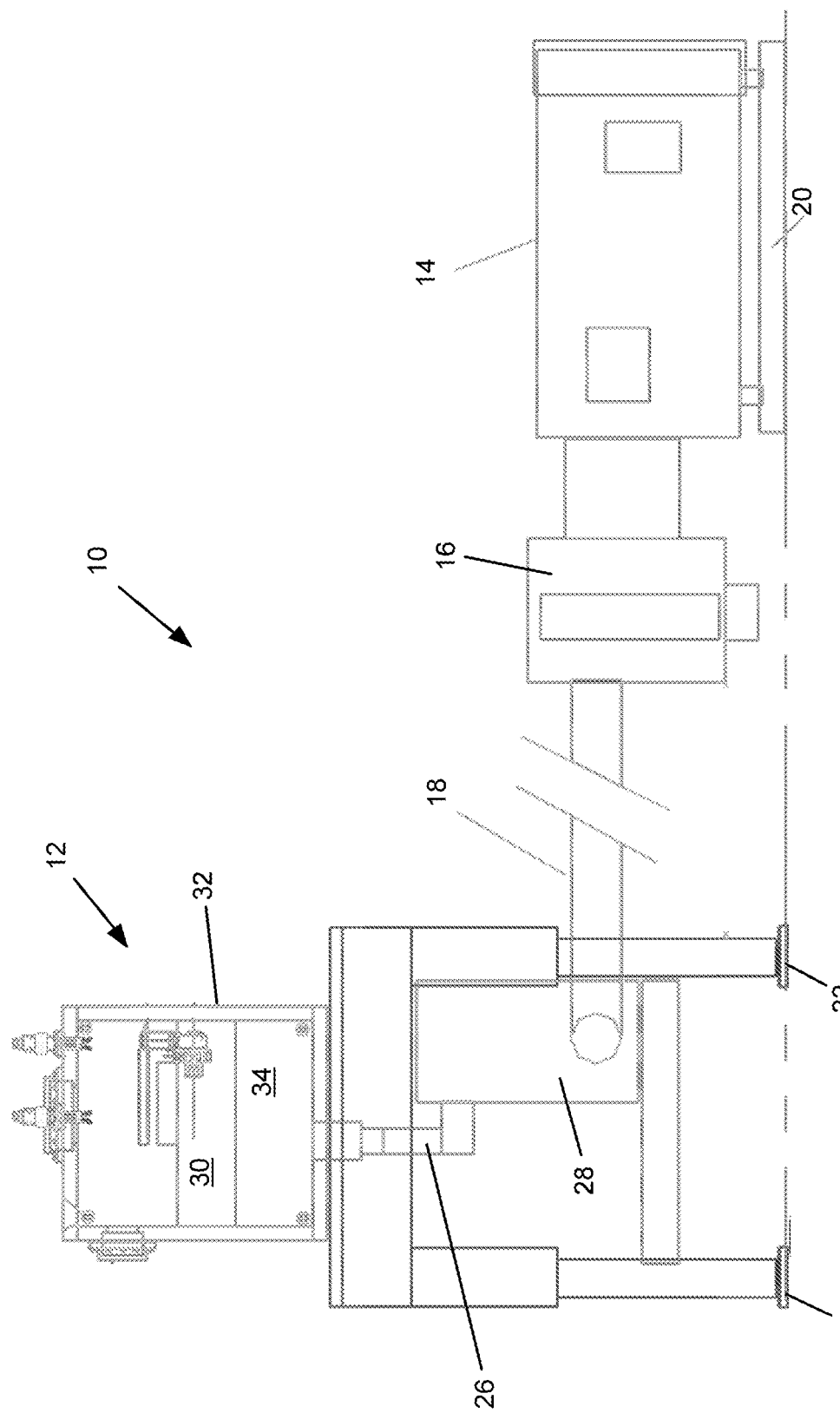
FIG. 2 schematically represents a detailed side view of the roll-to-roll freeze-drying system of FIG. 1A.
Figure 3:
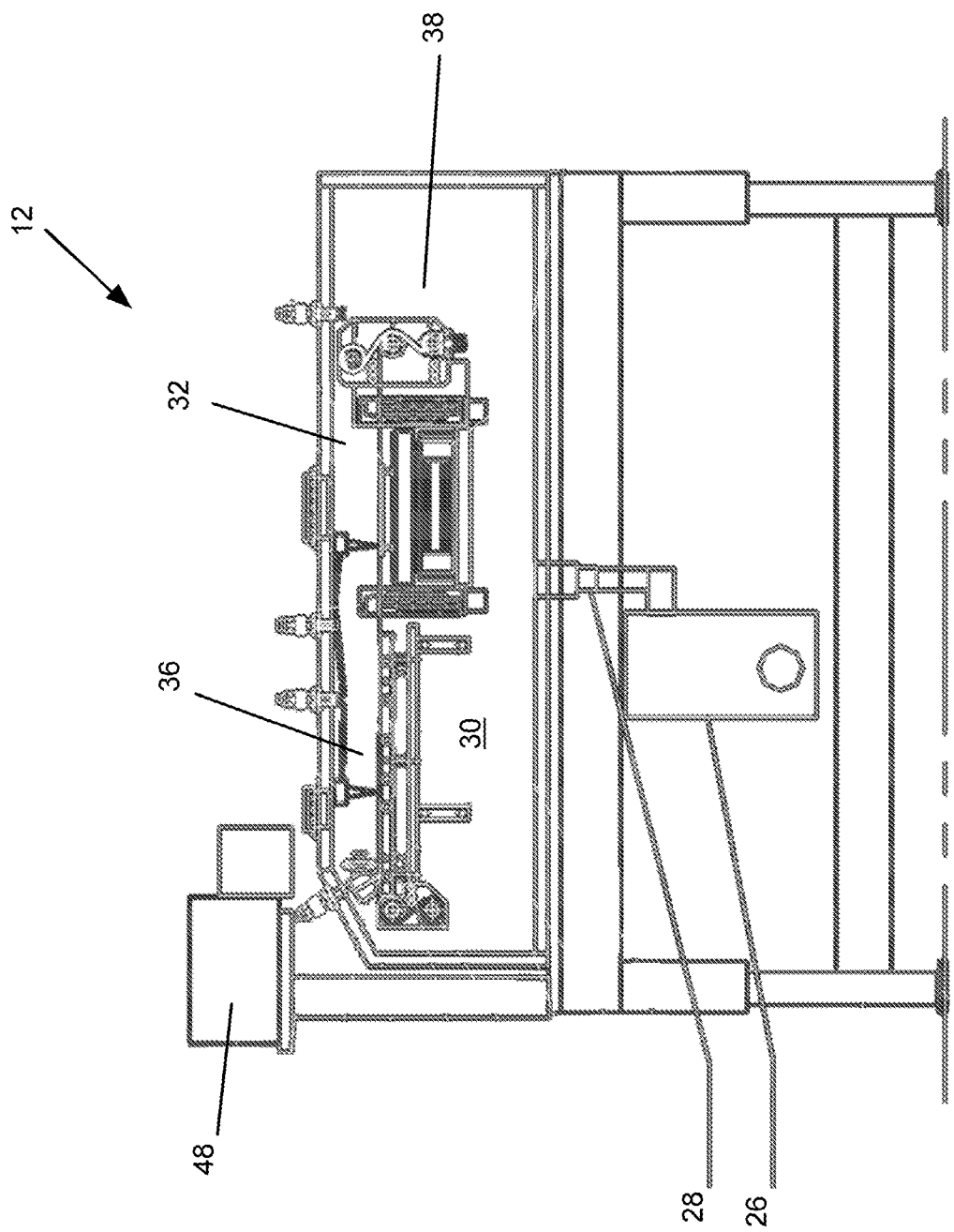
FIG. 3 schematically represents a detailed front view of the freeze-drying apparatus of FIG. 1B.
Figure 4:
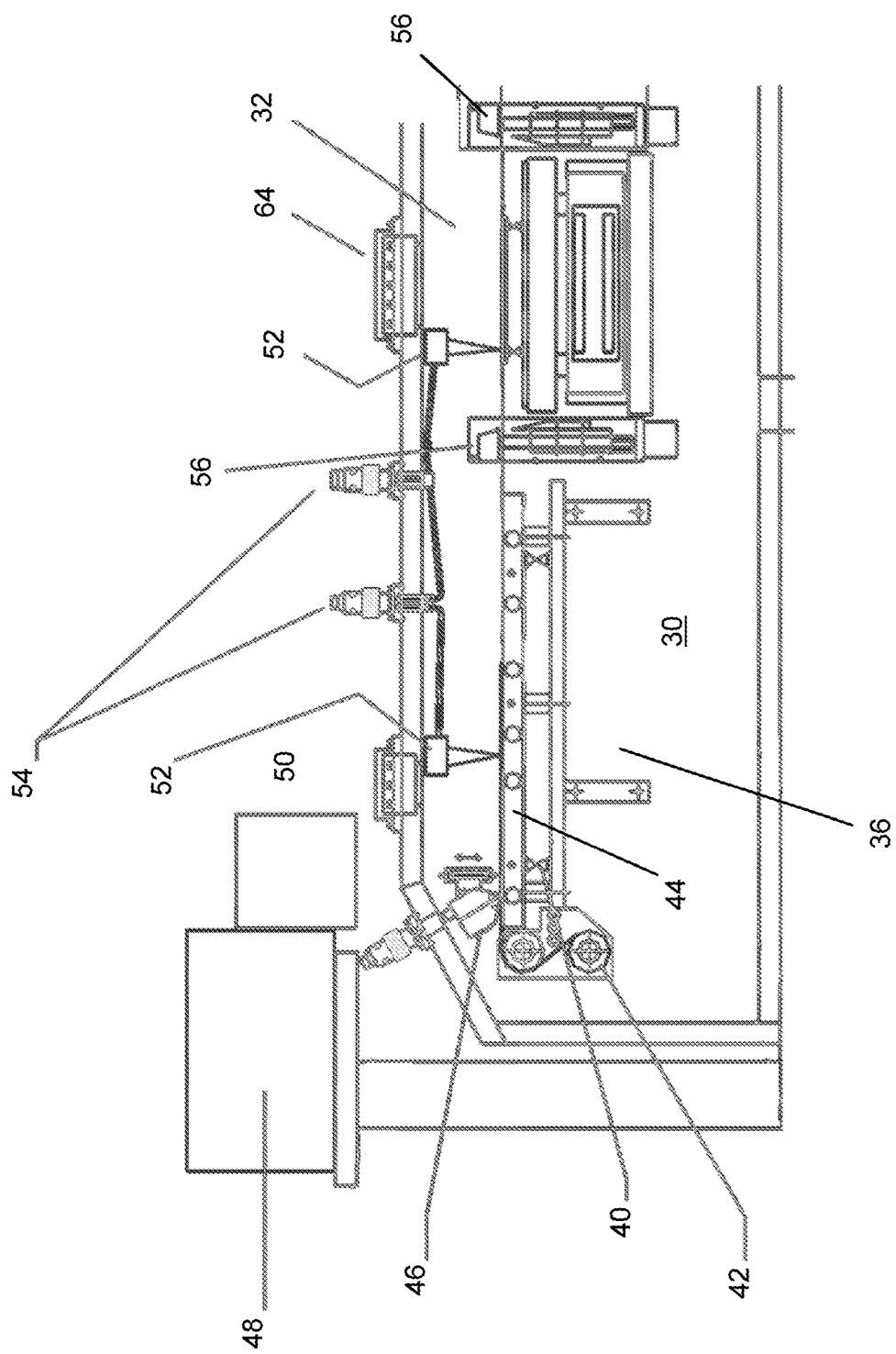
FIGS. 4 and 5 schematically represent detailed front views of a casting and freezing section of the freeze-drying apparatus of FIG. 3.

FIG. 1A schematically represents an overview of the system 10, including a freeze-drying apparatus 12 and a vacuum pump 14 connected to the apparatus 12, and FIG. 1B schematically represents an isolated front view of the apparatus 12. FIG. 2 provides a more detailed view of the system 10 as shown in FIG. 1A. The apparatus 12 provides the primary means by which the continuous freeze-drying process is performed, which generally involves dehydrating items by freezing them, and drawing a vacuum to reduce the pressure surrounding the items so that ice (and/or solids of other liquids frozen by the freezing step) is removed from the items by sublimation. These steps are performed in a main vacuum chamber 30 of the apparatus 12, where items are transformed into cast freeze-dried sheets following the removal of vapors released by sublimation. In the embodiment represented in the drawings, such an item may initially be in a liquid form that is dispensed on a substrate 40 fed from a feed roller 42 and while the substrate 40 is supported on a cooling plate 44, as depicted in FIG. 4. As will be discussed in reference to FIGS. 4 and 6, the apparatus 12 is also equipped to perform the collection of physical and chemical data relating to the freeze-drying process, which is primarily performed by a metrology section 32 and a mass spectroscopy system 34 of the apparatus 12.

The vacuum pump 14 is connected to the apparatus 12 to draw the necessary vacuum from the vacuum chamber 30 to maintain the chamber 30 and its contents in a vacuum, which as used herein means a sub-atmospheric pressure appropriate for the liquid to be freeze-dried. The pump 14 is connected through a condenser 16 that removes entrained vapors from air and gases drawn by the pump 14. The system 10 is further equipped with a cold stop 26 between the condenser 16 and an inlet 28 to the vacuum system. The inlet 28 is shown as located in close proximity to the metrology section 32, so that vapors can be rapidly extracted from the vacuum chamber 30 and condensed. The mass spectroscopy system 34 is also connected to the vacuum chamber 30 close to the metrology section 32 to analyze the vapors released by sublimation of the items being freeze-dried. The vacuum pump 14 can be of any suitable type, for example, an oil-less rotary vane vacuum pump. A flex vacuum line 18 provides the conduit for the air, gases, and vapors drawn by the pump 14, and is preferably of a type that inhibits the transmission of vibrations from the pump 14 to the apparatus 12. The pump 14 is represented as mounted on a damping baseplate 20 to further reduce the transmission of vibrations to the apparatus 12. The apparatus 12 is represented as similarly mounted on cushions to damp vibrations transmitted to the apparatus 12. Control of the system 10 is represented in FIG. 1A as being performed with an operator panel 24, which can be located remote from the system 10. In particular, the panel 24 can be used to control the freezing and sublimation processes carried out in the vacuum chamber 30, including programmable temperature and vacuum levels, as well as other operations described below.

Figure 5:
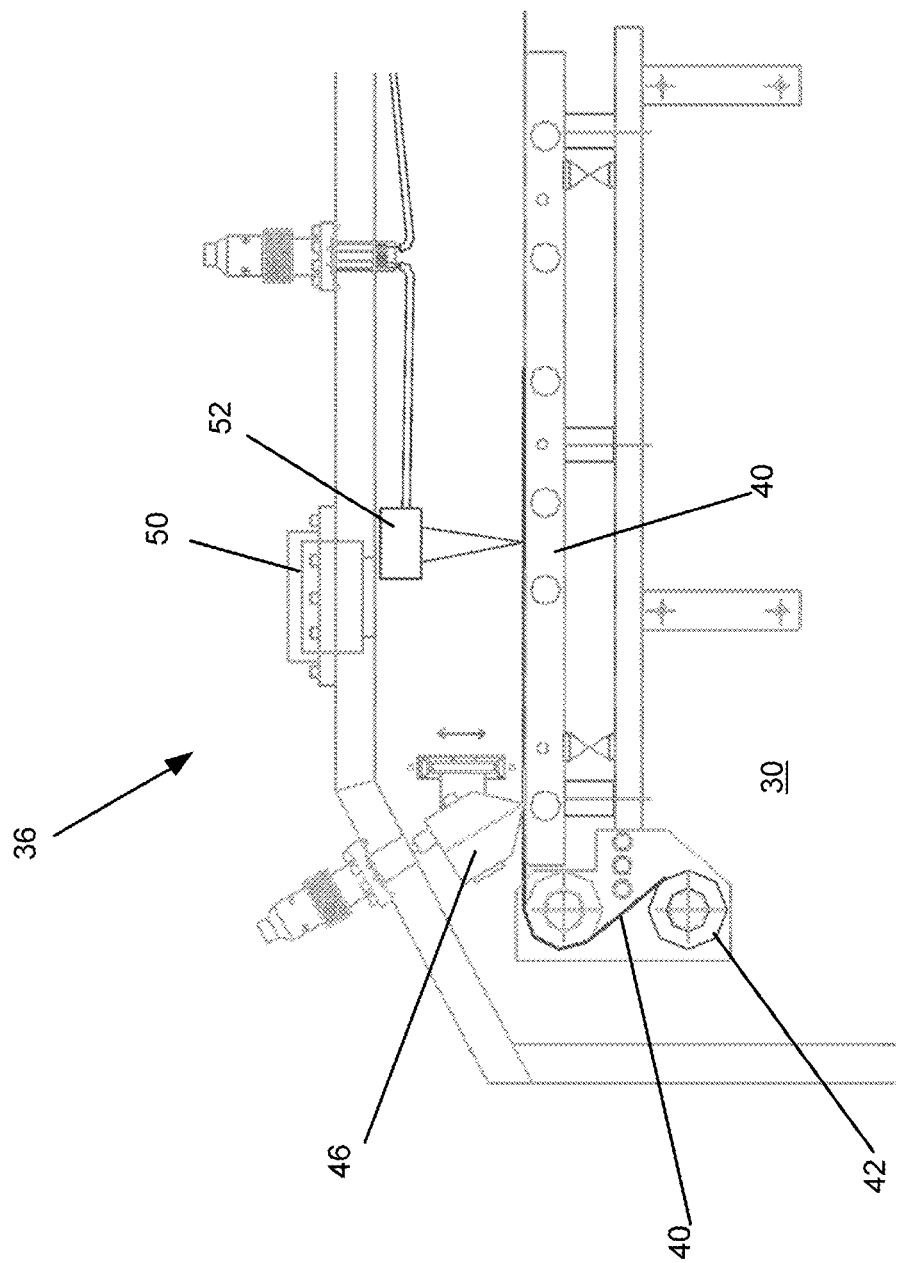

FIGS. 4 and 5 show details of a casting and freezing section 36 of the freeze-drying apparatus 12, in which the aforementioned substrate 40, feed roller 42, and cooling plate 44 are located. The feed roller 42 is part of a delivery system that dispenses the substrate 40 and continuously conveys the substrate 40 from the casting and freezing section 36 (FIGS. 4 and 5), through the metrology section 32 (FIGS. 4 and 6), and finally to a take-up section 38 (FIG. 7) of the apparatus 12. The substrate 40 may be any of various materials, a nonlimiting example of which is a moisture barrier film such as an aluminum-coated Mylar® (PET). The liquid to be freeze-dried is shown as delivered to the vacuum chamber 30 and dispensed on the substrate 40 through a slot die 46. The liquid, which may be a mixture, solution, emulsion, suspension, colloid, etc., is preferably deposited to form a film having a precise thickness, as nonlimiting examples, a thickness of about 0.1 mm or about 0.5 mm, though thinner and thick liquid films are also within the scope of the invention. Application of the liquid film may be performed with a patch coating apparatus, for example, coating equipment commercially available under the name WEBFLIGHT™ from Frontier Industrial Technology, Inc., of Towanda, Pa. USA. In addition to providing precise control of the liquid film thickness, such patch coating apparatuses can be used to precisely dispense on the substrate 40 discreet patches or islands of the liquid of a predetermined size and spacing therebetween, instead of a single continuous film. Prior to its application to the substrate 40, the liquid is preferably preconditioned in a preconditioning chamber 48 where gassing, degassing, and/or temperature control may be performed, depending on the liquid to be freeze-dried. Operators of the apparatus 12 may choose to control the amount of dissolved gasses in the incoming liquid, for example, by reducing or increasing the amount of dissolved gasses to reduce or promote bubble formation in the liquid as it enters the vacuum chamber 30. The liquid film is then carried by the substrate 40 away from the slot die 46 as the substrate 40 continues to be dispensed from the feed roller 42.

Figure 6:
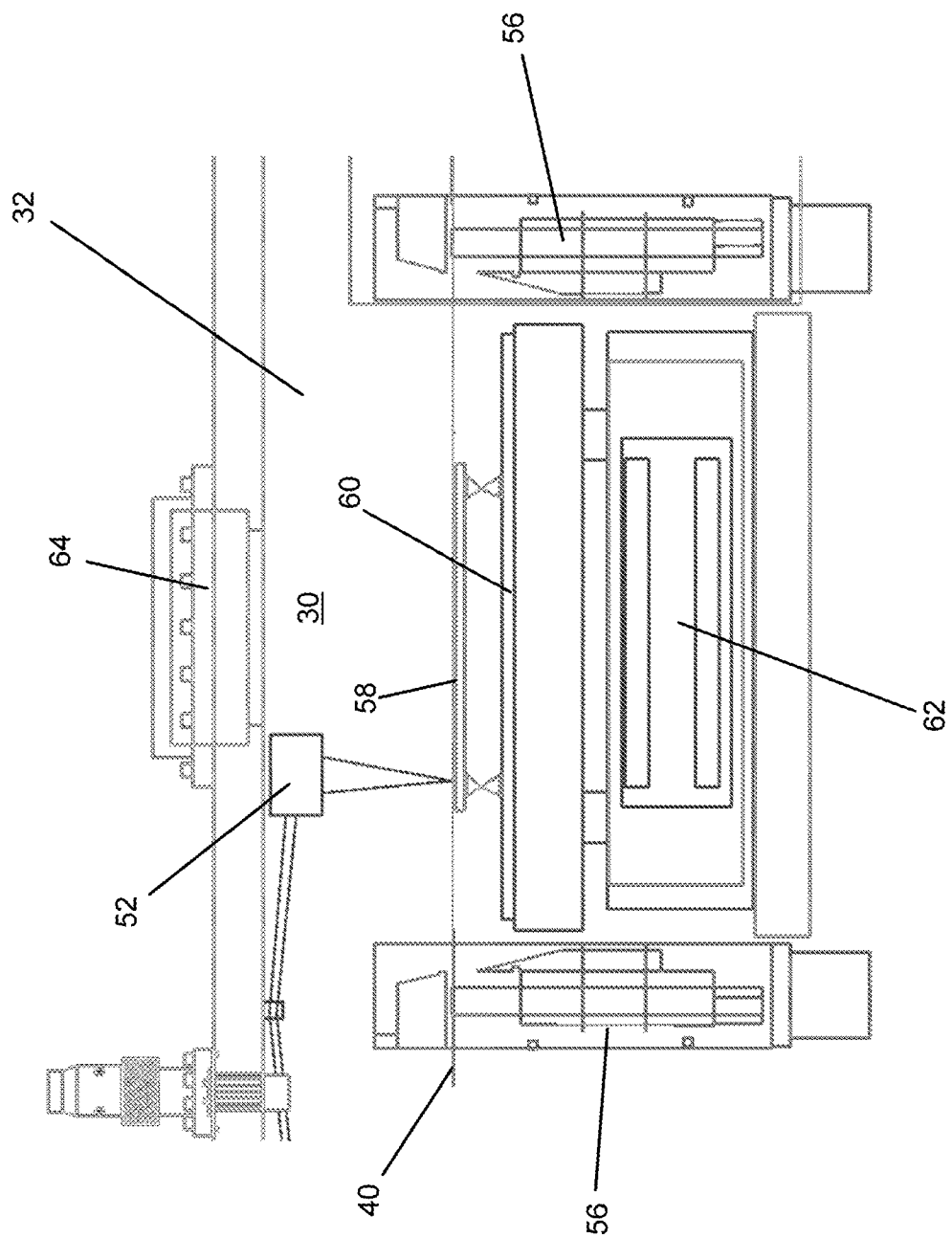
FIG. 6 schematically represents a detailed front view of a metrology section of the freeze-drying apparatus of FIG. 3.

Due to rapid cooling of the substrate 40 by the cooling plate 44, the thin liquid film is immediately frozen and then subjected to sublimation at programmed temperature and vacuum conditions within the vacuum chamber 30. Freezing of the liquid occurs due to direct thermal contact of the substrate 40 with the cooling plate 44, which may be, for example, cooled with liquid nitrogen. FIGS. 4 and 5 further depict an observation window 50 located downstream of the slot die 46 and immediately upstream of a laser thickness gauge 52. The window 50 may be equipped with a long-range microscopy system (not shown) to monitor the surface topology of the frozen sheet as it undergoes sublimation. Laser thickness gauges 52 are shown in the casting and freezing section 36 (FIGS. 4 and 5) and the metrology section 32 (FIGS. 4 and 6). In combination, the gauges 52 are employed as sensors to control the thickness of the freeze-dried sheet and monitor its change over time during sublimation to yield the freeze-dried sheet. Electrical connections to the gauges 52 are represented in FIGS. 4 and 5 through the wall of the chamber 30 by way of hermetic electrical feed-throughs 54.

FIG. 7 schematically represents the take-up section 38 of the apparatus 12, where the substrate 40 and the freeze-dried sheet borne thereon are drawn through the apparatus 12 by a driven rewinder roller 66. A rolled film payoff 70 delivers a film 68 to sandwich the freeze-dried sheet between the substrate 40 and film 68. Thereafter, sealing of the edges or dicing with patterned welding can be performed to create pouches, each encapsulating a premeasured amount of a freeze-dried portion of the freeze-dried sheet, that are suitable for distribution in the marketplace. Sealing can be performed by welding with a laser or by any other suitable means. These steps of the process can be facilitated with the use of the aforementioned patch coating apparatus, which forms discreet freeze-dried portions, spaced apart as individual islands on the substrate 40, that can be more readily individually encapsulated. The film 68 is preferably formed of a weldable material, for example, a moisture barrier film such as an aluminum-coated Mylar® (PET).

The processing steps described above are aspects of a first mode of operation for the system 10. This first mode can be employed as a continuous roll-to-roll production mode during which the liquid is dispensed and continuously frozen and dried to form the freeze-dried sheet, after which portions of the freeze-dried sheet are encapsulated in the take-up section 38 of the apparatus 12. The metrology section 32 allows the system 10 to operate in a second ("metrology") mode in which at least one freeze-dried sheet portion is cut from the freeze-dried sheet and conveyed into the metrology section 32 to undergo evaluation that generates physicochemical data that can be subsequently used to control the freezing and drying operations performed by the apparatus 12. As such, the metrology mode interrupts the conveyance of the substrate 40 through the apparatus 12.

FIG. 6 schematically represents the metrology section 32 as located within the chamber 30 immediately downstream of the casting and freezing section 36 depicted in FIGS. 4 and 5. The metrology section 32 is employed to obtain pristine physical and chemical data relating to the drying process occurring in the chamber 30. For this purpose, travel of the substrate 40 and the freeze-dried sheet borne thereon is paused for a period of time sufficient to bring the sheet to steady state, at which time two guillotines 56 are activated to cut a predetermined length of the substrate 40 and a portion of the freeze-dried sheet supported on the cut length of substrate 40. The substrate 40 and freeze-dried sheet portion then drop onto a platform 58 that sits on a heating/cooling plate 60, which in turn is supported by an electronic balance 62. The heating/cooling plate 60 may be a Peltier plate so as to be capable of being heated and cooled electronically, by which the temperature of the freeze-dried sheet portion can be controlled. A second observation window 64 is located immediately above the heating/cooling plate 60, and may be equipped with a long-range microscopy system (not shown) to monitor the surface topology of the freeze-dried sheet portion within the metrology section 32. The mass spectroscopy system 34 (FIG. 2) located below the metrology section 32 may utilize Raman spectroscopy in reflection mode, optical microscopy, etc., while the weight loss of the freeze-dried sheet portion due to sublimation is assessed by an electronic balance 62. In combination with the mass spectroscopy system 34, the metrology section 32 monitors various aspects of the freezing and sublimation processes, including the chemical composition of vapors released during the freezing and drying of the liquid, the weight and other physical characteristics of freeze-dried sheet portions at the conclusion of the sublimation process, etc., to generate physicochemical data that in turn can be utilized by the system 10 to control the freezing and drying of the liquid, for example, through control of the vacuum within the chamber 30 and the temperature of the plate 44 employed during the first mode of operation of the system 10.

Based on the above description, it is to be noted that using the methods and system 10 of this disclosure, a continuous freeze-drying process can be provided that facilitates more rapid freeze-drying of pharmaceuticals and food stuffs by casting and freezing a thin film of liquid, followed by sublimation at programmable temperature and vacuum levels.

While the present disclosure has been described with reference to a specific or particular embodiment, it should be apparent that alternatives could be adopted by one skilled in the art. For example, items other than those noted could be processed with the system 10, the system 10 and its components could differ in appearance and construction from the embodiment described herein and shown in the drawings, functions of certain components of the system 10 could be performed by components of different construction but capable of a similar (though not necessarily equivalent) function, process parameters could be modified, and various materials could be used in the fabrication of the system 10 and/or its components. In addition, the invention encompasses additional or alternative embodiments in which one or more features or aspects of a particular embodiment could be eliminated. Accordingly, it should be understood that the invention is not necessarily limited to any embodiment described herein or illustrated in the drawings. It should also be understood that the phraseology and terminology employed above are for the purpose of describing the illustrated embodiment, and do not necessarily serve as limitations to the scope of the invention. Therefore, the scope of the invention is to be limited only by the following claims.

The invention claimed is:

1. A continuous roll-to-roll freeze-drying process comprising:
   dispensing and continuously freezing and drying a liquid to form a freeze-dried sheet;
   encapsulating freeze-dried sheet portions of the freeze-dried sheet to create premeasured pouches containing the freeze-dried sheet portions; and
   monitoring any of the freeze-dried sheets and the freeze-dried sheet portions during the freezing and drying of the liquid to generate data for controlling the freezing and drying of the liquid.

2. The continuous roll-to-roll freeze-drying process of claim 1, further comprising:
   continuously conveying a substrate through a roll-to-roll freeze-drying apparatus;
   continuously depositing the liquid as a liquid film on the substrate; and
   immediately and continuously freezing the liquid film to form a frozen film.

3. The continuous roll-to-roll freeze-drying process of claim 2, further comprising monitoring chemical compositions of vapors sublimated during the drying of the liquid to generate further data for controlling the freezing and drying of the liquid.

4. The continuous roll-to-roll freeze-drying process of claim 3, wherein the roll-to-roll freeze-drying apparatus comprises a vacuum chamber in which the dispensing and continuous freezing and drying, the monitoring of the freeze-dried sheet and the freeze-dried sheet portions, the encapsulating, the conveying, and the monitoring of the chemical compositions are all performed in a sub-atmospheric pressure.

5. The continuous roll-to-roll freeze-drying process of claim 1, further comprising monitoring a film thickness of the liquid and the thickness of the freeze-dried sheet.

6. The continuous roll-to-roll freeze-drying process of claim 1, wherein the monitoring of the freeze-dried sheet and the freeze-dried sheet portions comprises at least one of monitoring a sublimation rate and weight changes of a frozen film of the liquid and the freeze-dried sheet.

7. The continuous roll-to-roll freeze-drying process of claim 1, further comprising monitoring surface topologies of a frozen film of the liquid and the freeze-dried sheet.

8. The continuous roll-to-roll freeze-drying process of claim 1, further comprising controlling gas content and temperature of the liquid prior to the liquid being dispensed, frozen, and dried.

9. The continuous roll-to-roll freeze-drying process of claim 1, wherein the process comprises first and second modes of operation, the first mode being a roll-to-roll production mode that comprises the dispensing and continuously freezing and drying of the liquid to form the freeze-dried sheet and the encapsulating of the freeze-dried sheet portions, and the second mode is a metrology mode in which at least one of the freeze-dried sheet portions is cut from the freeze-dried sheet, conveyed into a metrology section, and undergoes the monitoring to generate physicochemical data that is subsequently used to control the freezing and drying of the liquid during the first mode.

\* \* \* \* \*